(12) United States Patent
Salinas et al.

(10) Patent No.: US 10,537,695 B1
(45) Date of Patent: Jan. 21, 2020

(54) METHOD AND APPARATUS FOR CLEANING A TUBE

(71) Applicants: Jose Salinas, San Antonio, TX (US); Paul Bryce Martin, Jr., San Antonio, TX (US); John Thompson, San Antonio, TX (US)

(72) Inventors: Jose Salinas, San Antonio, TX (US); Paul Bryce Martin, Jr., San Antonio, TX (US); John Thompson, San Antonio, TX (US)

( * ) Notice: Subject to any disclaimer, the term of this patent is extended or adjusted under 35 U.S.C. 154(b) by 260 days.

(21) Appl. No.: 15/668,425

(22) Filed: Aug. 3, 2017

Related U.S. Application Data

(60) Provisional application No. 62/370,663, filed on Aug. 3, 2016.

(51) Int. Cl.
*B08B 9/043* (2006.01)
*A61M 16/04* (2006.01)

(52) U.S. Cl.
CPC ....... *A61M 16/0463* (2013.01); *B08B 9/0436* (2013.01)

(58) Field of Classification Search
CPC .......................... A61M 16/0463; B08B 9/0436
USPC ...................................................... 15/104.16
See application file for complete search history.

(56) References Cited

U.S. PATENT DOCUMENTS

| | | | | |
|---|---|---|---|---|
| 1,308,469 A | * | 7/1919 | Amet | F41A 29/02 15/104.16 |
| 1,733,512 A | * | 10/1929 | Parker | B08B 9/0436 15/104.31 |
| 2,018,124 A | * | 10/1935 | Forster | B08B 9/0436 15/104.19 |
| 2,157,493 A | * | 5/1939 | Miller | E21B 37/02 166/174 |
| 2,278,026 A | * | 3/1942 | Smith | E03F 9/002 15/104.31 |
| 2,395,019 A | * | 2/1946 | Sievers | B08B 9/0436 15/104.19 |
| 4,502,482 A | * | 3/1985 | DeLuccia | A61M 16/04 128/207.14 |
| 4,827,553 A | * | 5/1989 | Turpin, Sr. | B08B 9/0436 134/21 |
| 6,775,872 B1 | * | 8/2004 | Appleton | B08B 9/0436 15/104.16 |
| 8,157,919 B2 | * | 4/2012 | Vazales | A61B 1/0669 134/8 |
| 8,381,345 B2 | * | 2/2013 | Vazales | A61B 1/126 15/104.05 |
| 8,382,908 B2 | | 2/2013 | Vazales et al. | |
| 8,458,844 B2 | | 6/2013 | Vazales et al. | |
| 8,468,637 B2 | | 6/2013 | Vazales et al. | |
| 8,534,287 B2 | | 9/2013 | Vazales et al. | |
| 8,601,633 B2 | | 12/2013 | Vazales et al. | |
| 8,650,696 B1 | * | 2/2014 | Morales | B08B 9/0436 15/104.14 |
| 2006/0130251 A1 | * | 6/2006 | Bourrelly | B08B 9/021 15/104.09 |
| 2011/0023888 A1 | | 2/2011 | Vazales et al. | |

(Continued)

*Primary Examiner* — Marc Carlson
(74) *Attorney, Agent, or Firm* — Shah IP Law, PLLC; Samar Shah

(57) ABSTRACT

An umbrella-like scraper for cleaning tubes and pipes may include a scraper, an actuator and a hinge configured for selective deployment of the scraper by manipulation of the actuator.

3 Claims, 11 Drawing Sheets

(56) References Cited

U.S. PATENT DOCUMENTS

2011/0240058 A1\* 10/2011 Jonassen ............... B08B 9/0436
134/8
2013/0228196 A1  9/2013  Vazales et al.

\* cited by examiner

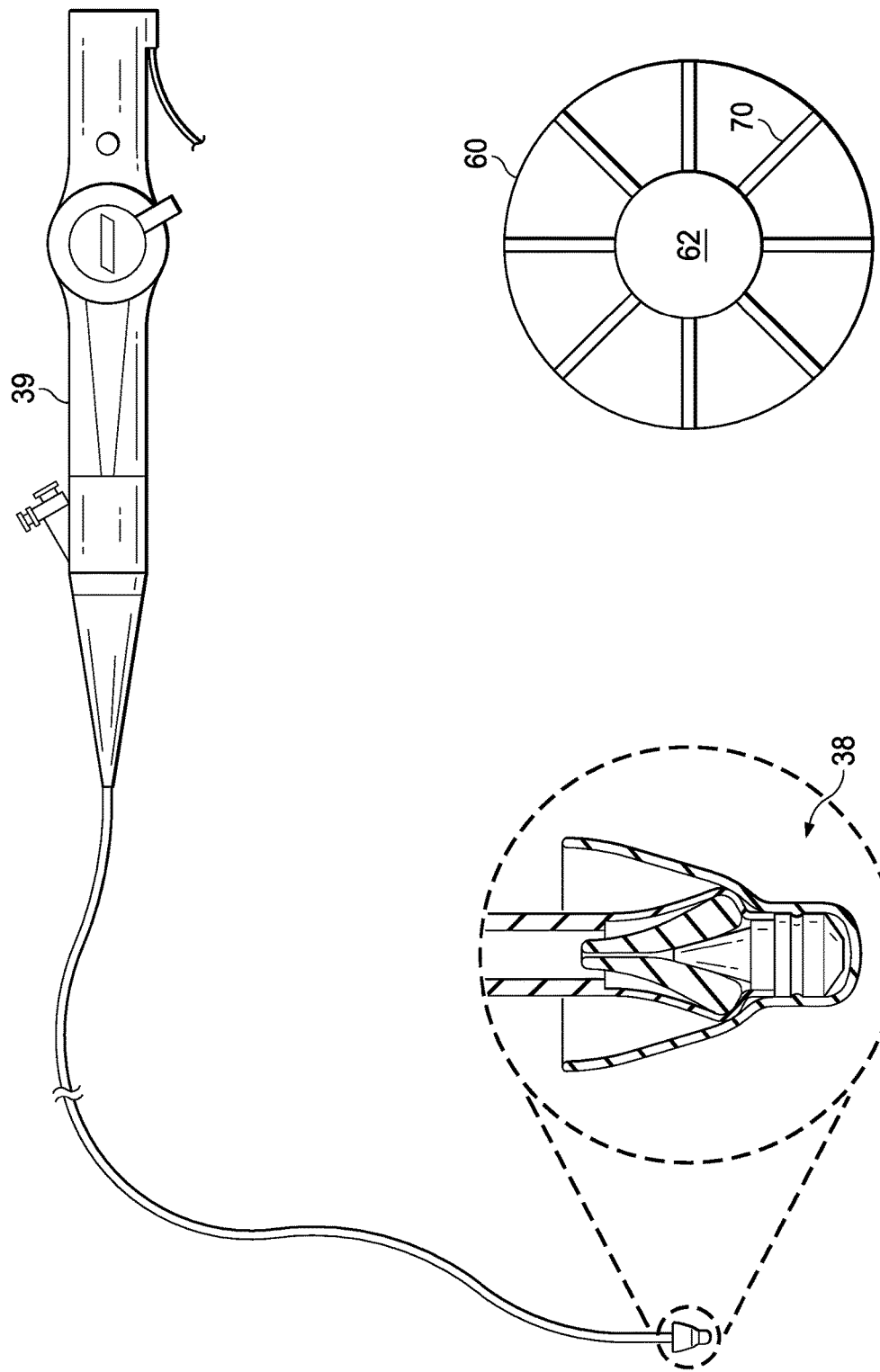

US 10,537,695 B1

METHOD AND APPARATUS FOR CLEANING A TUBE

CROSS-REFERENCE TO RELATED APPLICATION

This application claims priority to U.S. Provisional Patent Application No. 62/370,663 entitled "METHOD AND APPARATUS FOR CLEANING A TUBE OR PIPE" filed Aug. 3, 2016, the disclosure of which is hereby entirely incorporated herein by reference.

FIELD

The disclosed method and apparatus generally relate to methods and apparatuses for in situ cleaning a tube, and more particularly for the cleaning of body-inserted tubes used in medical procedures, as well as to other methods and apparatuses for removing fluids, secretions and/or other materials from such tubes.

SUMMARY

An umbrella-like scraper for cleaning tubes and pipes may include a scraper, an actuator and a hinge configured for selective deployment of the scraper by manipulation of the actuator.

BRIEF DESCRIPTION OF THE DRAWINGS

FIG. 4A illustrates an umbrella scraper containing reinforcing ribs.

FIG. 4B illustrates a tube scraper deployed on an endoscope.

DETAILED DESCRIPTION

Figure 1:
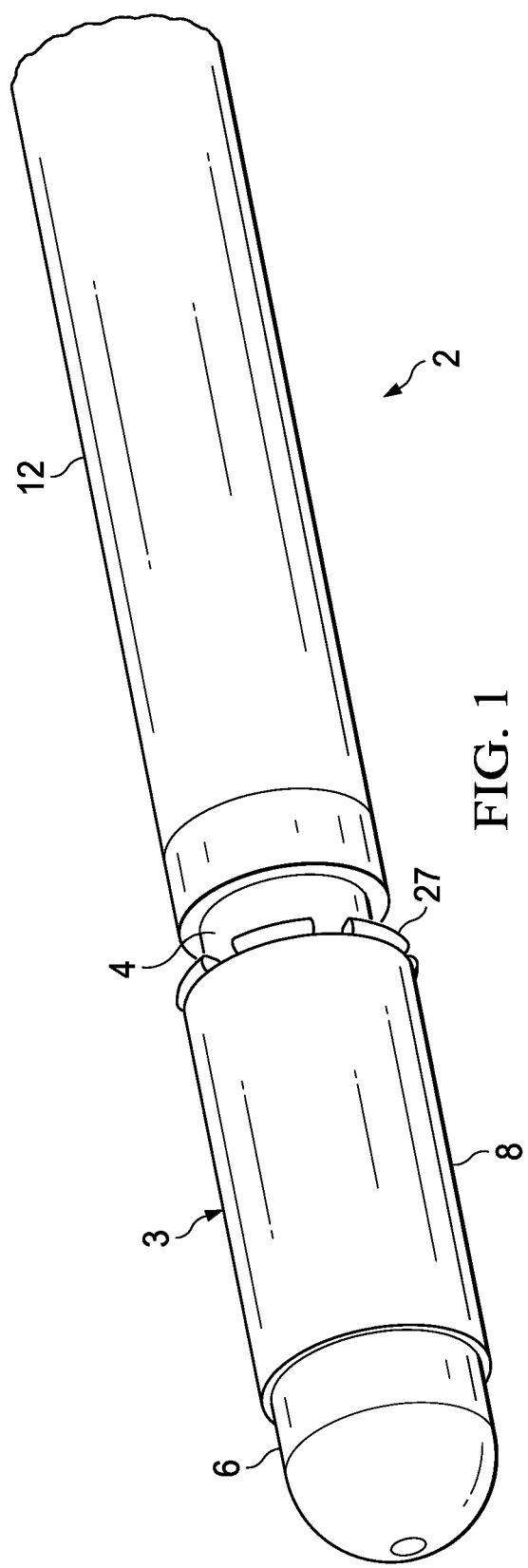
FIG. 1 illustrates an embodiment of tube cleaner.
Figure 2:
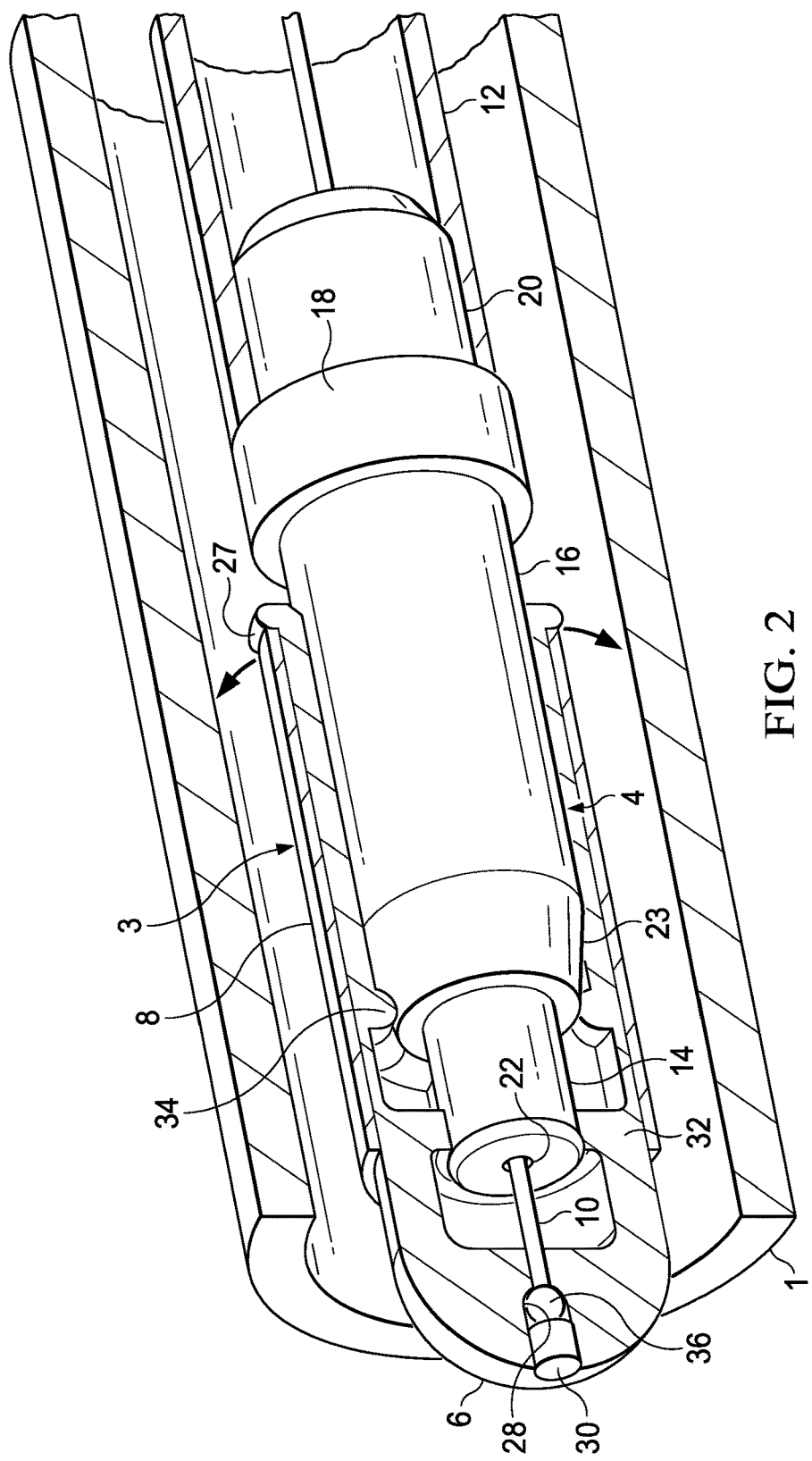
FIG. 2 illustrates a partial section view of a tube cleaner deployed in a tube with the scraper arms retracted.
Figure 2A:
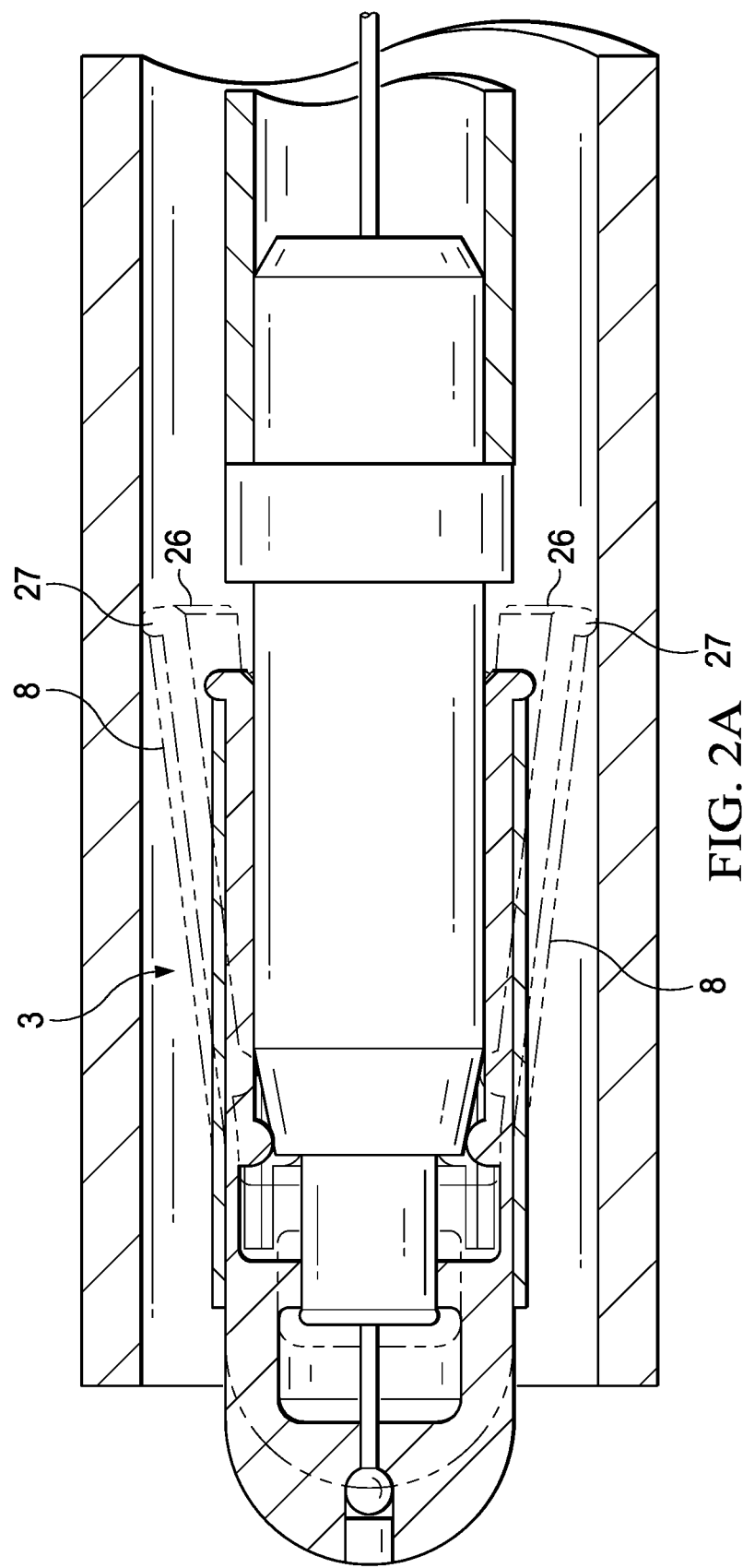
FIG. 2A illustrates a tube cleaner deployed in a tube with the scraper arms extended.
Figure 3:
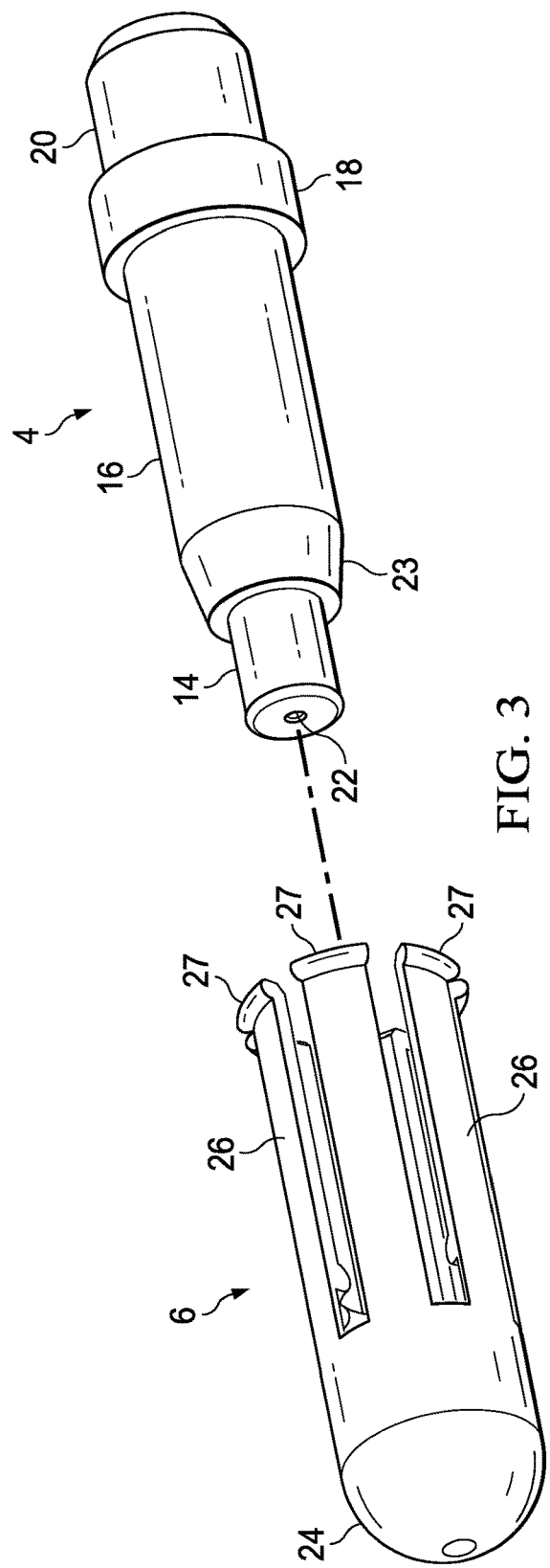
FIG. 3 illustrates an embodiment of a cleaning head in an exploded view.

As seen in FIGS. 1-3, one embodiment of a tube cleaner 2 may comprise a cleaning head 4, umbrella scraper 3, a deployment actuator 10, and a tubular translation sheath 12 configured for insertion into a tube or pipe 1, such as an endotracheal tube, for cleaning out any detritus, mucus, biofilm, debris, or other unwanted material that may have accumulated in the tube.

The cleaning head 4 may be the element of the tube cleaner 2 at which the other major elements connect, interact, and are disposed. In one embodiment, with further reference to FIG. 3, the cleaning head 4 may be semi-cylindrical body comprised of a forward nose 14, core 16, retaining shoulder 18, and a sheath landing 20. The core 16 may form a passageway 22 through the length of the core 16, such as along the central axis, so as to allow the actuator 10 to traverse the core 16 and communicate with the scraper armature 6. In the disclosed embodiment, the cleaning head comprises a round radial cross-section, but may alternatively comprise a polygonal radial cross-section.

In one embodiment, the retaining shoulder 18 may be disposed the length of the core 16 from the proximal end of the core 16, such as approximately one-quarter of the length thereof from the proximal end, and may, along with the sheath landing 20, be configured to receive the translation sheath 12. The sheath landing 20 generally comprises the area of the core 16 from the retaining shoulder 18 to the proximal end of the core 16. This proximal end of the landing 20 may be beveled so as to prevent a sharp edge against the sheath 12 when the cleaning head 4 is mated with the sheath 12. In other embodiments, the core 16 may not include a retaining shoulder 18. In yet further embodiments, the core may be integrally formed with the translation sheath 12.

Additionally, the core 16 may have a beveled edge at the distal end of the core 16 so as to create a cam guide surface 23 as a path for the umbrella scraper 3 to travel along as the umbrella 3 is extended and retracted by translation with respect to the core 16. This guide path creates the expanding and contracting motion of the umbrella scraper 3 as the armature 6 moves along the cam guide surface 23.

The forward nose 14 may be of a diameter smaller than the major diameter of the core 16, and may be disposed at the distal end of the core 16. The nose 14 may serve as the seat for the scraper armature 6. The end of the nose 14 may form an opening of the core passageway 22. The end of the sheath landing may form another opening (not shown) of the core passageway 22.

In some embodiments, the umbrella scraper 3 may be comprised of a scraper armature 6 and a scraper shroud 8. The scraper armature 6 may then be comprised of a nose section 24 and two or more scraper arms 26. The nose section 24 may maintain a retaining seat 28 for seating of the actuator 10. The retaining seat 28 may be sealed with a tip plug 30 disposed into an opening in the tip of the nose section 24. Behind the retaining seat 28 for the actuator 10, there may be an internal collar 32 for coactive reception with the nose 24 of the cleaning head 4. The arms 26 of the scraper armature 6 may originate at or near the collar 32. Each arm 26 may include a cam ridge 34 disposed such that the cam ridge 34 rests at the start of the cam guide surface 23 when the arms 26 are in the retracted position. The cam ridge 34 may traverse the cam guide surface 23 of the cleaning head 4 during deployment or retraction of the scraper armature 6.

The actuator 10 may be flexible, such as a cable, or may be rigid, such as a rod. The actuator 10 may be coupled to the nose section 24 in any suitable manner, such as by adhesive or integral formation with the nose section 24. The deployment action may be achieved by manipulation of the actuator 10. Such a manipulation may entail pulling on the actuator 10 through the core 16 so as to move the collar 32 along the nose 14 of the cleaning head 4, while relaxing tension on the actuator 10, or pushing on the actuator 10 may result in the retraction of the scraper arms 26. In some embodiments, the scraper shroud 8 may comprise an elastomeric material that stretches upon deployment, and provides a biasing force to urge the armature arms to a retracted position.

In various embodiments, the scraper armature 6 may rest along or adjacent the surface of the core 16 when in the retracted position, and may pivot away from the core 16 to place the scraper shroud 8 and the leading edge of the armature 6 in contact with the inner wall surface of the tube 1 to be cleaned. Ideally, the armature may be orientated such that in the expanded configuration, the umbrella scraper forms a concave cone in relation to the distal end of the tube 1. Alternately, the umbrella scraper may open to form a convex cone in relation to the tube 1. When expanded, said contact may include the entirety of the inner wall surface circumference or an arcuate section thereof. Full circumferential contact may form a sealed extraction path from the point of deployment of the arms 26 to the exit point of the tube 1 to be cleaned.

With further reference to FIG. 3, the scraper arms 26 may be made from a rigid or semi-rigid material so as to create a scraping action with the edge of the scraper shroud 8 as the tube cleaner 2 is translated along the length of the tube 1 to be cleaned and the arms 26 are in the extended position. The arms 26 may, in some embodiments, include a ridge at the proximal end of the arms 26 so as to aid in the cleaning process. The arms 26 may be present as two or more arms (as shown in FIG. 3), and in a single set of arms (as shown in FIG. 3) or multiple sets of arms in series (not shown). In some embodiments, multiple sets of arms 26 may be disposed in series along the disclosed cleaning head 4 so as to improve efficacy during a single cleaning cycle. These arms 26 may be of a length suitable for a particular diameter of tube 1 to be cleaned or may be configured so as to adjust to multiple tube diameters. To aid in the efficacy of the scraping process or to better retain a scraper shroud 8, the arms 26 may form a scraping ridge 27 at or near the terminal edge of the arm 26. In some embodiments, the scraper shroud may be formed as part of the scraper armature, and may comprise a web of material between two or more of the arms.

In some embodiments, the scraper shroud 8 may be a thin walled cylinder of high elasticity that may be disposed over the scraper armature 6. Said shroud 8 may be of a natural or synthetic polymer or rubber, elasticized cloth, or other material of an elasticity that may aid in the retraction of the arms 26. Such a scraper shroud 8 may comprise a separate structure added to the scraper armature 6, or may comprise a coating added to the scraper armature 6, or may be formed as part of the scraper armature 6. The scraper shroud 8 may serve one or more functions in the tube cleaner 2. For example, the scraper shroud 8 may aid in the scraping process, and to provide a surface to catch and control any material freed from the walls of the tube being cleaned. The scraper shroud 8 may form an impenetrable barrier between the scraper armature 6 and the tube wall, thus substantially preventing loosened debris from passing through the tube cleaner 2 and contaminate the cleaned section of the tube or infiltrate into a patient. Moreover, shroud 8 elasticity may aid in returning the arms 26 to the retracted position when the actuator 10 is manipulated so as to retract the tube cleaner 2 from deployment.

There may be an actuator 10 to transfer the afore described pushing and pulling user input to the scraper armature 6. Such an actuator 10 may be connected to the retaining seat 28 of the scraper armature 6 and the actuator 10 may then extend through the central axis passageway 22 of the core 16, through the inner length of the translation sheath 12, and then exit the open end of the sheath 12 to allow the user to apply the pushing and pulling forces. The actuator 10 may be a cable of sufficient stiffness to transfer the applied forces from the user to the armature 6. The cable stiffness may also allow the cable to flex while not kinking or binding during operation. Alternately, the actuator 10 may be a rod, series of linked rod sections, a wire, a string, or other linkage system that may accurately transfer the user input to the cleaning head 4. The actuator 10 may terminate in a ball 36. This ball 36 may mate into the retaining seat 28 and act to provide the reactive force against the scraper armature 6 used to configure the arms 26 into the expanded cleaning position when the actuator 10 is manipulated to do as such. In some embodiments, the actuator may be used to move the armature between a retracted position and a single deployment position. In other embodiments, the actuator may be used to move the armature between a retracted position and one or more of a plurality of deployment positions. A plurality of deployment positions may be used to adjust the force with which the scraper shroud 8 presses against the inner diameter of the tube to be cleaned. When the tube cleaner is deployed, the actuator may be locked against translation with respect to the cleaning head (such as by clamp or latch to the translation sheath) so as to more easily permit translation of the tube cleaner in the tube to be cleaned.

The translation sheath 12 may represent the component by which the user translates the tube cleaner 2 through the tube 1 to be cleaned. By pushing or pulling the sheath 12, the user may advance or retract the tube cleaner 2 along the length of the tube 1 to be cleaned. This translation sheath 12 may be a formed of flexible tubing such that the sheath 12 maintains an elasticity appropriate to allow the sheath 12 to slightly stretch when mating to the cleaning head 4 and then attempt to constrict onto the sheath landing 20 so as to maintain linkage as the tube cleaner 2 is translated through the tube that is to be cleaned. The sheath 12 may be semi-rigid so as to not crumple, kink, or otherwise bind when force is applied to the sheath 12 during movement through the tube 1 to be cleaned. The sheath 12 may also maintain graduated markings along the length of the sheath 12 so as to allow the determination of insertion depth into the tube 1 to be cleaned.

The tube scraper 2 may be disposable in the entirety, wherein the user employs a completely new tube scraper 2 in whole at each use, or individual components may be considered disposable. For example, in a setting that does not require the disposal of the entire scraper 2 after a single use, the umbrella scraper may be the only component that needs to be changed between uses. The user would disconnect the umbrella scraper from the actuator and from the cleaning head. A new umbrella scraper 3 would then be attached prior to further use. Alternately, the scraper shroud 8 may be the only section of the umbrella scraper 3 that requires disposal after a single use. In some situations or settings, it may be deemed necessary to replace the cleaning head and scraper umbrella. In such scenarios, the cleaning head 4 may be detached from the translation sheath 12 and the actuator 10 detached from the umbrella scraper 3. A new set of components may then be attached prior to subsequent use.

Figure 4:
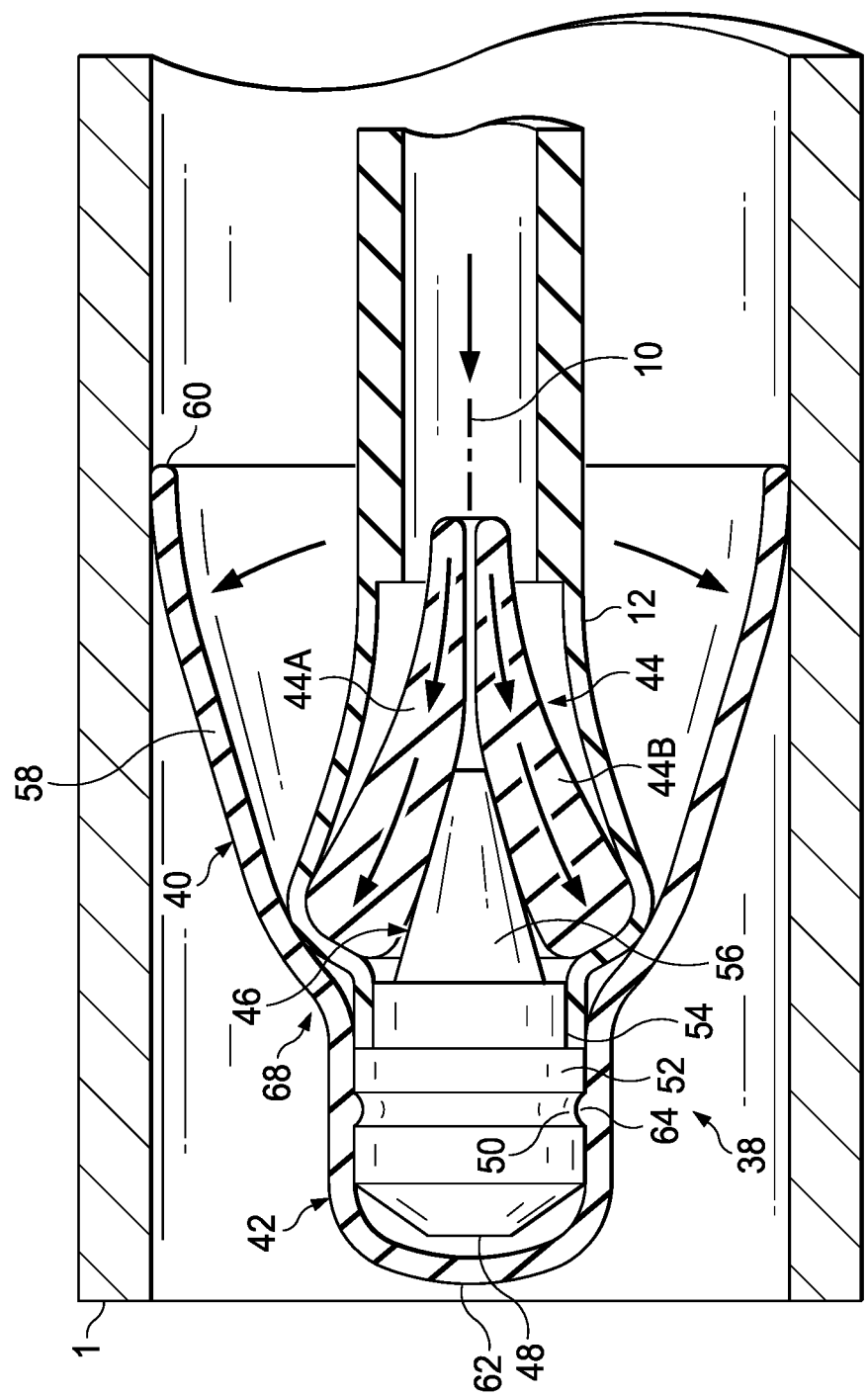
FIG. 4 illustrates another embodiment of a tube cleaner.
Figure 5:
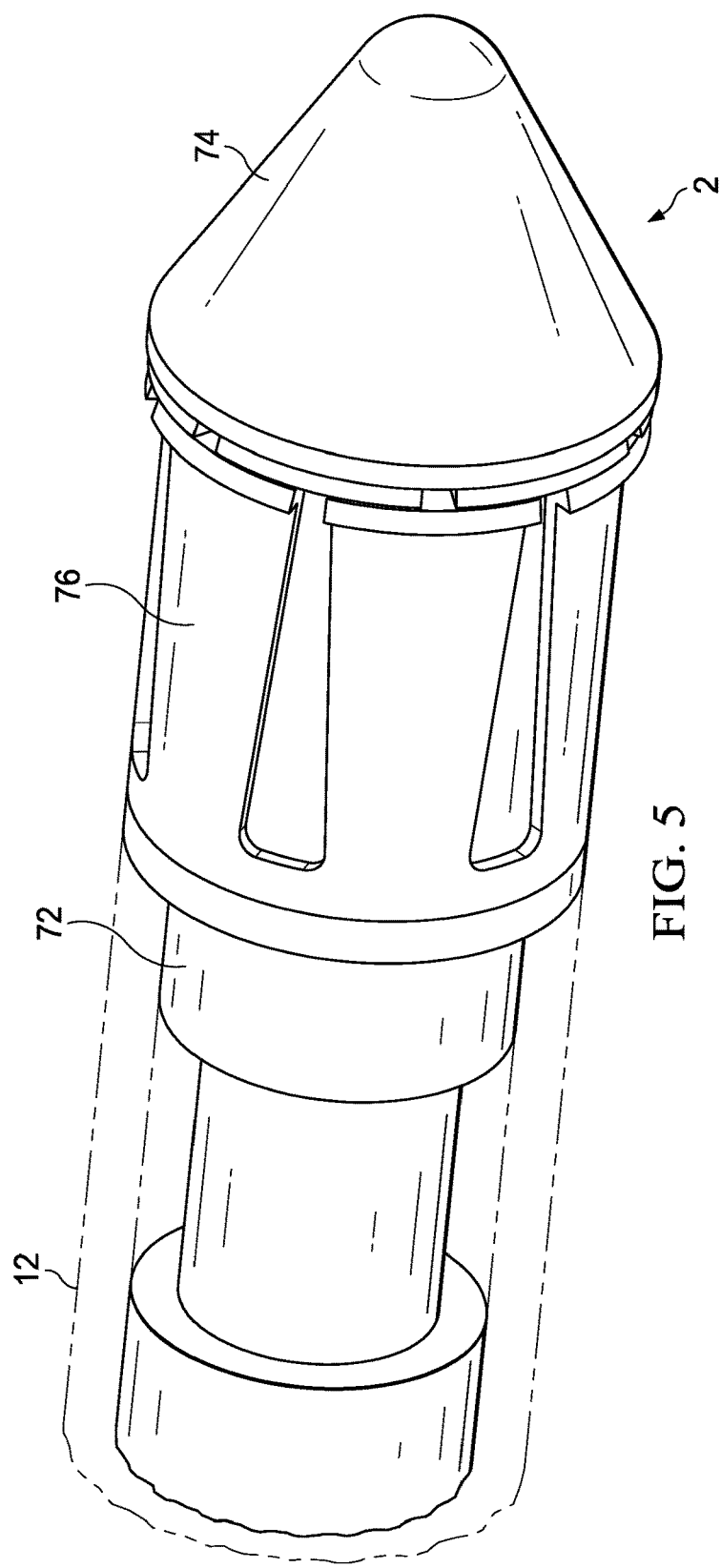
FIG. 5 illustrates another embodiment of a tube cleaner.

In another embodiment, as seen in FIG. 4, the tube cleaner 2 may comprise a cleaning head 38, an umbrella scraper 40, an actuator 10, and a translation sheath 12 so as to be able to be inserted into a tube can then clean out any detritus, mucus, biofilm, debris, or other unwanted material that may have accumulated in the tube.

The cleaning head 38 may be the element of the tube cleaner 2 at which the other major elements connect, interact, and are disposed. This cleaning head 38 may be further comprised of sub-components to include a mating head 42 and an actuation cam 44. The mating head 42 may be the point at which the umbrella scraper 40 attaches to the cleaning head 38. The mating head 42 may include a cam guide surface 46 against which the actuation cam 44 may seat and actuate along while the actuation cam 44 induces the expansion and contraction of the umbrella scraper 40. In some embodiment, the actuation cam 44 may comprise one or more cam lobes 44A and 44B.

Such a mating head 42 may have a rounded distal nose 48 that is followed by a mating groove 50. This groove 50 may allow for removably secure coupling of the umbrella scraper 40 to the cleaning head 38, as described in more detail below. The mating groove 50 may be followed by a shoulder 52 of substantially the same outside diameter of as the largest outside diameter of the nose 38. The shoulder 52 may then be followed by a landing 54 of smaller diameter than the shoulder 52. This landing 54 may be the point at which the translation sheath 12 mates with the cleaning head 38. The translation sheath 12 may be disposed over the landing 54 until the sheath 12 abuts the shoulder 54. Frictional forces between these components may keep the cleaning head 38 from disengaging from the sheath 12. The sheath 12 may also have a smaller inner diameter than the outer diameter of the landing 54 so that the sheath 12 also applies a compressive force onto the landing 54 to further ensure that the sheath 12 remains in place. In some embodiments, a clip, weld, adhesive or other means may be used to permanently or temporally retain the sheath 12 to the cleaning head.

The mating head 42 may further comprise a tapered or curved cone 56. The cone 56 may function as a wedge against which to operate the actuation cam 44 of the cleaning head 38. The cone 56 may provide the cam guide surface 46 along which the actuation cam 44 translates.

The actuation cam 44 may comprise a split cam seated over the tapered cone 56 of the cleaning head 38. The actuation cam lobes 44A and 44B may each be tapered such that the distal end of the actuation cam 44 is larger than the proximal end of the actuation cam 44. Such a taper may allow the distal end of the actuation cam 44 to push the arm section 58 of the umbrella scraper 40 when the actuation cam 44 and the tapered cone 56 are urged together such that the cam lobes 44A and 44B move along the cam guide surface 46. Translation of the cam lobes 44A and 44B move along the cam guide surface 46 results in the cam lobes 44A and 44B moving apart, thereby urging the arm section 58 to pivot toward the inner wall of the tube 1. This push on the arm section 58 may cause the umbrella scraper 40 to enlarge in diameter until the leading edge 60 of the umbrella scraper 40 is in contact with the inner wall surface of the tube and applying adequate force against the wall so as to effectively scrape off the targeted materials. The actuation cam 44 and the tapered cone 56 may be urged together by pulling the cam guide surface 46 of the mating head 43 into the cam 44, or by pushing the cam 44 onto the cam guide surface 46. Accordingly, the actuator 10 may be configured for coupling to the mating head 42 or cam 44 as may be suitable for the force vector to be applied.

For example, if a pulling force is exerted on the actuation cam 44, the actuation cam lobes 44A and 44B will then translate down the cam guide surface 46 of the tapered cone 56 of the mating head 42 and thus allow the arm section 58 of the umbrella scraper 40 to retract towards the cleaning head 38. As such, the leading edge 60 may no longer be in contact with the inner surface of the tube wall and the tube cleaner 2 may be freely translated along the length of the tube without inducing any material removal from the tube wall.

There may be an actuator 10 to transfer the afore described pushing and pulling forces to the actuation cam 44. Such an actuator 10 may be connected to the proximal end of the actuation cam 44 and the actuator 10 may then extend the inner length of the translation sheath 12 to the open end and allow the user to apply the pushing and pulling forces. The actuator 10 may ideally be a cable of sufficient stiffness to transfer the applied forces from the user to the actuation cam 44. The cable stiffness may also allow the cable to flex while not kinking or binding during operation. Alternately, the actuator 10 may be a rod, series of linked rod sections, a wire, a string, or other linkage system that may accurately transfer the user input to the cleaning head 38.

Alternately, the actuation cam 44 may be actuated by a fluid, such as air or water. In such an embodiment, the actuation cam 44 may be a sac or bladder of elasticity and the actuator 10 may be take the form of a compressive band or device which causes the sac or bladder to expand radially when compressed, or a fluid delivery device such as a tube or pipe. In this embodiment, to expand the scraper arm section 58, fluid may be delivered into the actuation cam 44 via the delivery device 10. As the actuation cam 44 fills, the actuation cam 44 will begin to expand in volume and thus push the scraper arms 58 outward and into contact with the tube wall that is to be cleaned. In such an embodiment, the cam guide surface 46 need not be tapered.

The translation sheath 12 may be a formed of flexible tubing such that the sheath 12 maintains an elasticity appropriate to allow the sheath 12 to slightly stretch when mating to the cleaning head 38 and then attempt to constrict onto the landing 54 so as to maintain linkage as the tube cleaner 2 is translated through the tube that is to be cleaned. The sheath 12 may be semi-rigid so as to not crumple, kink, or otherwise bind when force is applied to sheath 12 during movement through the tube 1 to be cleaned.

As previously disclosed, the cleaning head 38, namely the mating head 42, may support an umbrella scraper 40. Such an umbrella scraper 40 may comprise a separate structure added to the cleaning head 38, or may comprise a coating added to the cleaning head 38, or may be formed as part of the cleaning head 38.

Such an umbrella scraper 40 may perform the delodging, removal, scraping off, and transfer of undesired materials inside the tube 1 to be cleaned. The umbrella scraper 40 may be a semi-rigid material such that an arm section 58 of the umbrella scraper 40 does not crumple, crush, bind, or otherwise fail during operation of the tube cleaner 2. The umbrella scraper 40 may have a belled nose 62 which may fit over the mating head 42 of the cleaning head 38. An inner ridge 64 may be disposed at the terminus of the belled region 62 such that the ridge 64 couples with the mating groove 50 of the mating head. Said ridge 64 may form a "quick release" coupling between the mating head 42 and umbrella scraper 40. In other embodiments, this "quick release" coupling may be realized through a threaded connection, bayonet connector, two-part clam shell, or other snap-fit modality as known to one skilled in the art.

The belled nose 62 of the umbrella scraper 40 may be followed by a cylindrical section of the umbrella scraper 40. The cylindrical section may continue from the inner ridge 64 to where the actuation cam 44 of the cleaning head 38 contacts the umbrella scraper 40. A flexure bearing 68 may be disposed at the contact point such that the following arm section 58 of the umbrella scraper 40 may retract and extend dependent on the action of the actuation cam 44. Said flexure bearing 68 may be a living hinge wherein the material of the shroud may be thinned or cut so as to flexure at the desired location. Alternately, said flexure bearing 68 may be an articulated hinge wherein independent members are joined with a geometry such that the individual section couple together and allow pivotal motion about the axis of the coupling point.

The arm section 58 may, in some embodiments, perform a cleaning action for the tube cleaner 2. The leading edge 60 of the arm section 58, as seen at the terminus of the arm section 58, may be used as a scraping surface. Reinforcing ribs 70 (as shown in FIG. 4A), similarly as to in a rain umbrella, may be disposed circumferentially in the arm section 58 if the arm section 58 is constructed of a material that cannot maintain the desired form without further reinforcement. Any suitable number of ribs may be used. Additionally, an umbrella scraper 40 formed of a material lacking an elasticity high enough to fully contract the arm section 58 may benefit from the reinforcing ribs 70. For example, a polymer shroud may not require the ribs to maintain the desired form, while an umbrella scraper 40 mainly formed of a cloth may benefit from addition reinforcement. Said ribs 70 may be disposed about the central axis of the cleaning head 38 in a circular pattern. The flexural rigidity or elasticity of the arm section 58 and reinforcing ribs 70 may induce the retraction of the umbrella scraper 40 when the actuator 10 is pushed with a forward motion or tension is released from the actuator 10.

As seen in FIG. 4B, the cleaning head 38 may be separated from the translation sheath 12 and attached to another device 39, such as an endoscope. The endoscope 39 may then serve as the delivery and actuation vehicle such as the translation sheath 12 would be in normal use. For example, fluid may be provided through a lumen of an endoscope 39.

In another embodiment, as seen in FIGS. 5-8, the tube cleaner 2 may comprise a cleaning head 72, forward nose cone 74, umbrella scraper 76, and a translation sheath 12 configured for insertion into a tube (not shown) and then clean out any detritus, mucus, biofilm, debris, or other unwanted material that may have accumulated in the tube.

Figure 6:
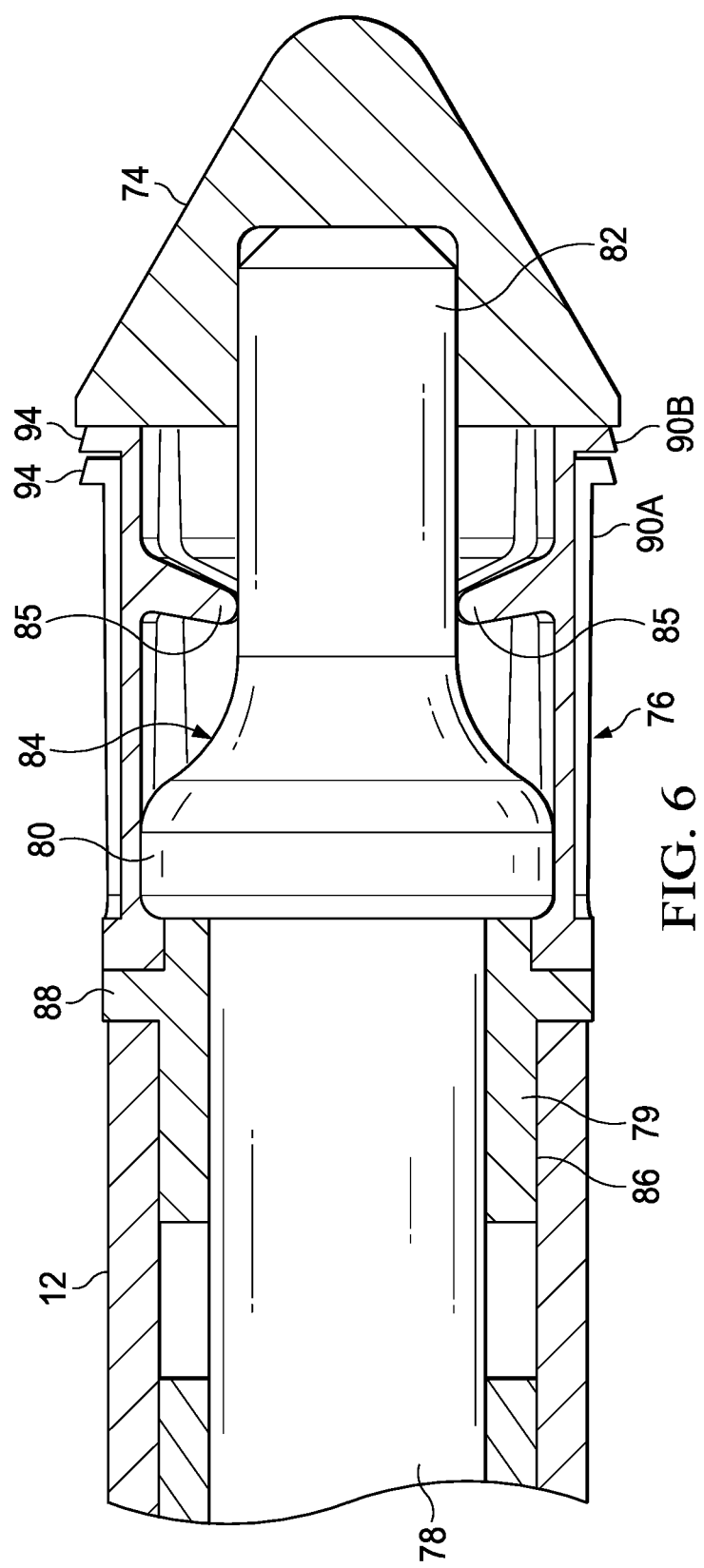
FIG. 6 illustrates a partial section view of a tube cleaner.
Figure 7:
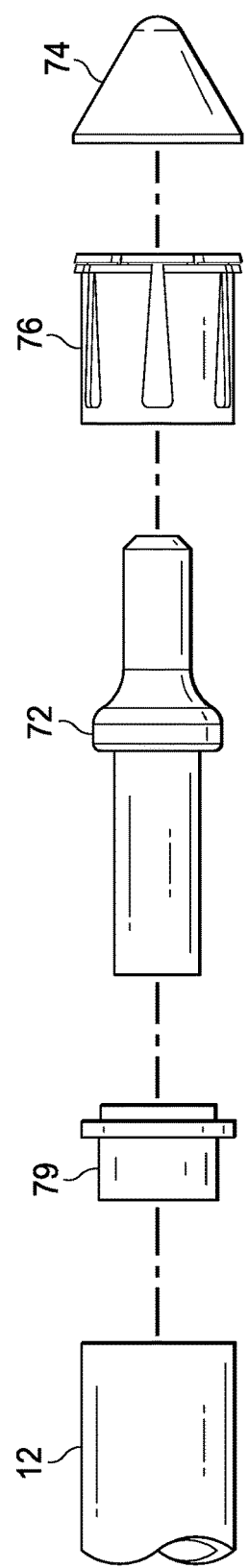
FIG. 7 illustrates an exploded view of an embodiment of a tube cleaner.
Figure 8:
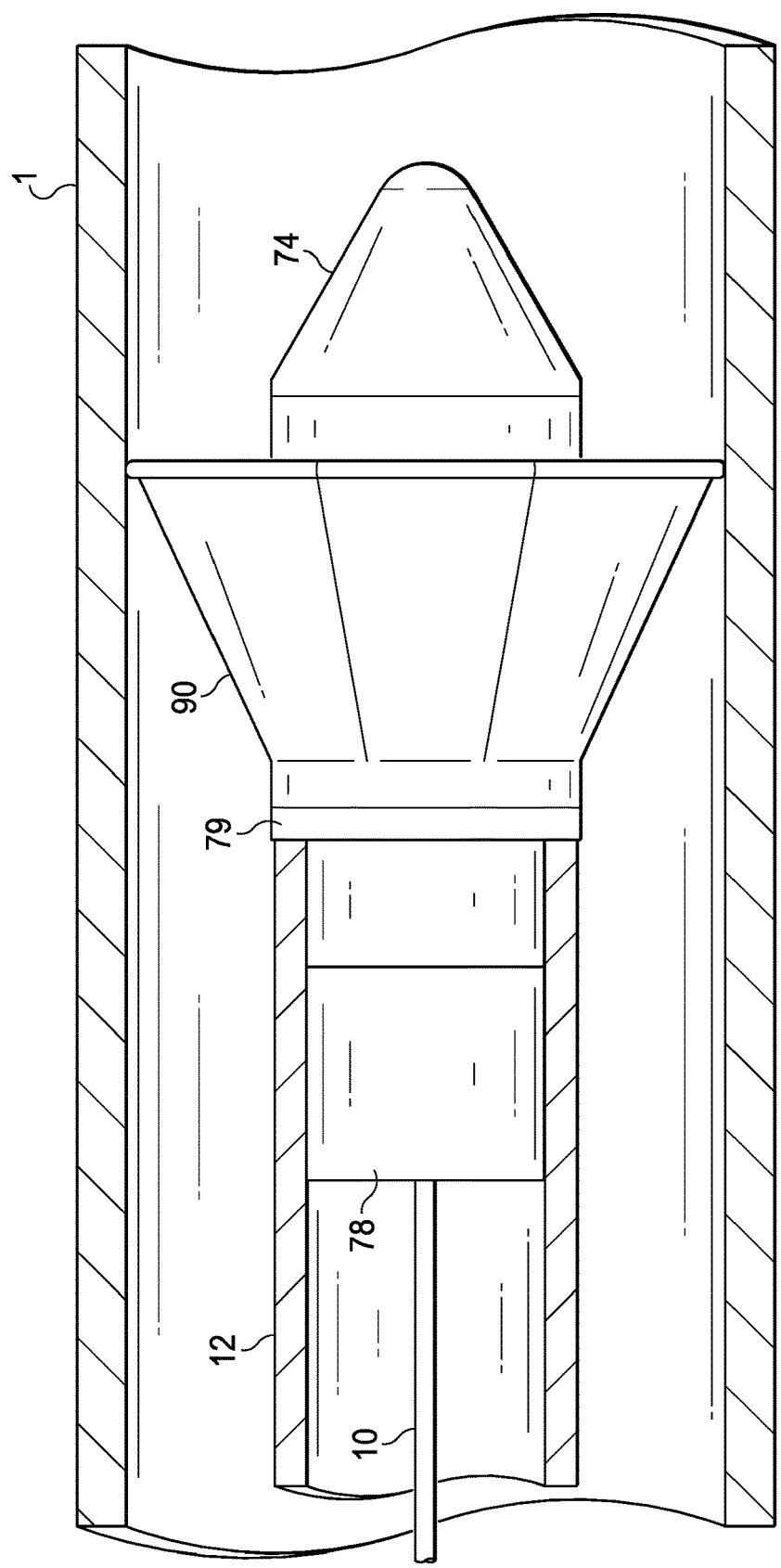
FIG. 8 illustrates a tube cleaner deployed in a tube with the scraper petals extended.
Figure 9B:
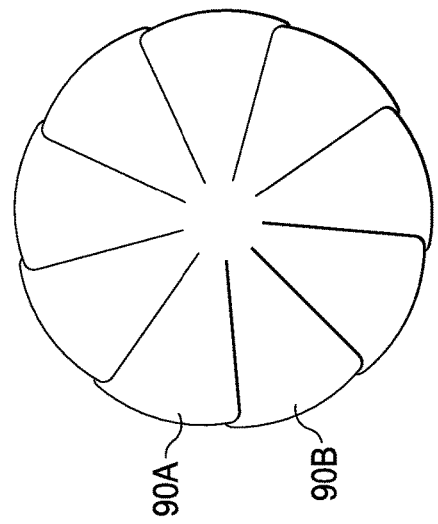
FIGS. 9A-9D illustrate an umbrella scraper in the extended and retracted positions.
Figure 9D:
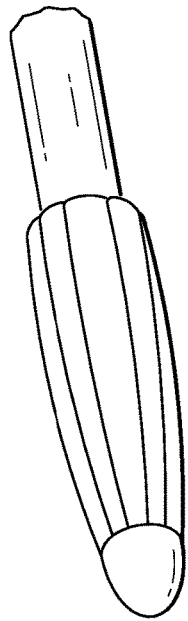
Figure 9A:
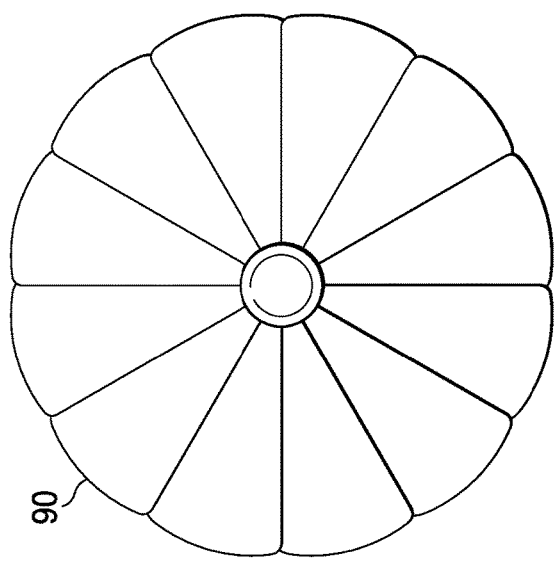
Figure 9C:
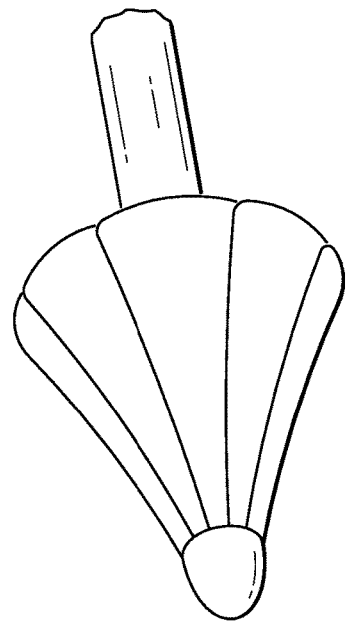

With reference to FIG. 6, the cleaning head 72 may be the element of the tube cleaner 2 at which the other major elements connect, interact, and are disposed. The cleaning head 72 may further comprise a rear actuator 78, stop collar 79, shoulder 80, and forward nose 82. The rear actuator 78 may be the element that transmits user input into the cleaning head 72 so as to achieve a particular umbrella scraper 76 configuration. This rear actuator 78 may be a cylindrical body over which the stop collar 79 may seat. The translation sheath 12 may be disposed over or about the actuator 78 and abut at the shoulder collar 88. The stop collar 79 may abut the umbrella scraper 76 and serve to limit the translation distance of the rear actuator 78.

The shoulder collar 88 may be of a larger diameter than the rear actuator 78 with a substantially flat perpendicular face at the junction with the rear actuator 80. This substantially flat perpendicular plane may be followed by a substantially flat face parallel the tube 1 to be cleaned so as to form the shoulder 80. This shoulder 80 may have a sloped face going toward the forward nose 82 so as to act as a cam guide surface 84 along which the actuation cam ridges 85 of the scraper body may translate and induce the deployment (expansion) and retraction of the umbrella scraper 76. Translation of the shoulder 80, as induced by the rear actuator 78, may force cam ridges 85 in the umbrella scraper 76 to travel along the slope of the actuation cam guide surface 84 and so affect the expansion and retraction of the umbrella scraper 76. As in previous embodiments, the umbrella scraper 76 may open to form a concave cone in relation to the distal end of the tube 1. Alternately, the umbrella scraper may open convex to the distal end of the tube 1, and the deployment mechanism suitably configured according to the teachings hereof to permit such deployment.

In some embodiments, the umbrella scraper 76 may be a petalled armature. In the embodiment of FIG. 6, the armature may comprise a mating neck 86, shoulder collar 88, cam ridges 85, and overlapping petals 90. The mating neck 86 may be a hollow cylindrical body such that the neck 86 may fit over the rear actuator 78 and the neck 86 may terminate into the shoulder collar 88. The shoulder collar 88 may be the element of the umbrella scraper 76 which serves as the stop for the shoulder 80 of the cleaning head 72 and the element from which the overlapping petals 90 originate. The proximal vertical face of the umbrella scraper 76 may be the abutment point for the translation sheath 12 should the sheath 12 be seated so far forward.

The overlapping petals 90 may form the umbrella scraper 76 in such a manner so as to negate the need for the use of a shroud as seen in other embodiments, although such a shroud may be optionally used. In some embodiments, an armature may comprise petals instead of ribs. Said petals 90 may increase in width from the juncture at the shoulder collar 88 and extending towards the terminus of the petals 90. The petals 90 may also maintain a rigid leading edge along the circumference of the umbrella scraper 76 so as to aid in the cleaning process. Such an edge may maintain a circumferential ridge 94 that is beveled to create a sharp edge for removing unwanted material from the inner wall surface of the tube 1 to be cleaned. When in the retracted position, the petals 90 may partially or wholly overlap one another such that there is a repeating pattern of upper petal 90A and lower petal 90B wherein the upper petals 90A lie on top of the lower petals 90B. When retracted, the petals 90 may lie behind the rear edge of the nose cone 74. In the extended position, the leading edges of the petals 90 may abut or partially overlap so as to create a single leading edge of the scraper 76. Alternately, the petals 90 may not alternate in height but overlap one another such that one edge in under the preceding petal while the counter edge sits on top of the following petal. Such a design can be seen in FIGS. 9A-9D along with illustrations of the umbrella scraper 76 in the extended and retracted position. In some embodiments, the petals may be configured for deployment by translational motion of an actuator, or by rotational motion of an actuator.

A method for cleaning a tube, such as an endotracheal tube, may comprise inserting the tube scraper into the open end of the tube that is away from the patient. With the scraper armature in the retracted state, the tube cleaner may then be transited to the distal end of the endotracheal tube or to a first major occlusion in the tube. The movement of the tube cleaner through the tube may be realized by applying a pushing force to the translation sheath of the tube cleaner. Such a force may transit the tube cleaner though the endotracheal tube without engaging the arms of the scraper armature.

When the tube cleaner is in the desired location along the length of the tube, a pushing force may then be applied to the actuator so as to extend the scraper armature and thus engage the umbrella scraper with the inner wall of the tube. Once engagement has been achieved, a pulling force may be applied to the translation sheath so as to draw the tube cleaner away from the distal end of the tube. This action may cause the leading edge of the scraper shroud to scrape off any foreign material that has accumulated inside of the tube. As this foreign material is scraped from the inner wall of the tube, the material may become entrapped by the tube cleaner and thus be drawn out of the tube back toward the open end of the tube into which the tube cleaner has been inserted. This may act to prevent debris infiltration into undesired regions, such as a patient or device coupled to the tube at the opposing end of the tube. Whether to push or pull on the translation sheath depends on whether the scraper is to exit the proximal or distal end of the tube. Such a decision may rest upon many factors, one such being what lies at the distal end of the tube. For example, if the tube is inserted into a patient and is being cleaned without removal from the patient, then debris would need to be removed from the proximal end of the tube by pulling the translation sheath (regardless of whether the umbrella opens toward the distal or toward the proximal ends of the tube or pipe to be cleaned), whereas if the tube was disconnected from the patient then the debris may be safely removed from either end of the tube. In other embodiments, a reciprocating push/pull force may be used to repeatedly scrape the umbrella against matter more firmly lodged on the inner wall of the tube.

Upon egress of the tube cleaner from the open end of the tube, the entire tube cleaner may either be cleaned or replaced and the process repeated until the tube is free of foreign matter to the desired level. Rather than disposing or cleaning the apparatus, the user may opt to remove the cleaning head and either clean or replace the head and as another option, the scraper cover may be removed and either cleaned or replaced.

In a healthcare environment, for example, the tube cleaner as described herein may be used in place of any closed-suction device between the ventilator circuit and the endotracheal tube during normal patient care. Depending on the institutional policies and procedures, for example, the tube cleaner may be used multiple times a day or disposed and replaced after each use. When clinicians suspect severe airway obstruction caused by secretion buildup, the tube cleaner can be used as a rescue catheter without changing devices or altering the steps followed for routine airway clearance.

In the case of cleaning an endotracheal or ET tube, for example, a clinician may insert the distal end of the tube cleaner into an ET tube having a biofilm buildup. The distal end may be advanced into the ET tube a desired distance. The tube cleaner may be deployed by operating the actuator so as to linearly compress the umbrella scraper of the tube cleaner and cause the arms to flare out and create a disc. Such compression may be effected until the scraper shroud expands to contact the inner diameter of the ET tube. The clinician may then translate the tube cleaner in the ET tube to pull biofilm out of the end of the proximal end of the ET tube. The actuator may thereafter be released to allow the arms and scraper shroud to collapse. The process may be repeated until the ET tube has been cleaned to a desired degree.

Thus, a cleaner for a tube (endotracheal or otherwise) may comprise of an umbrella scraper, actuator, and a translation sheath. The umbrella scraper may comprise a cleaning head and scraper armature. The scraper armature may be disposed at the distal end of the cleaning head with the cleaning head disposed at the terminus of the translation sheath. The actuator may be connected to the scraper armature, routed through the cleaning head, and in turn transit through the translation sheath such that the actuator exits the translation sheath at the user end of the sheath.

The scraper armature may comprise a plurality of arms such as to create an umbrella-like frame work of ribs over which the scraper shroud may be disposed. The arms may converge at central point where at the actuator may be linked to the scraper armature. The scraper may be compressed so as to expand the umbrella to any suitable diameter. The diameter of the umbrella may be determined based on the length and configuration of the scraper. Longer ribs may allow the umbrella to expand to a greater diameter than shorter ribs. In other embodiments, the combination of the umbrella mechanism or petal length and deployment angle may allow for a single size for multiple types of tubes. Conversely, the umbrella mechanism or petal length could be implemented for optimal use on a tube of a single size. Thus, the umbrella scraper may be suitably configured for deployment in any tube diameter. Decompression or relaxation of the scraper may allow the umbrella to relax, thus collapsing the umbrella after deployment. The resulting cone can have the open end facing either the distal or proximal end of the tube to be cleaned, and the deployment mechanism suitably configured according to the teachings hereof to permit such deployment.

The actuator may retract and expand arms of the scraper armature to configure the device for different steps of the cleaning procedure. The retracted state of the arms may be achieved by applying a pushing force to the actuator while the expanded state of the arms may be achieved by applying a pulling force on the actuator.

Retraction of the arms may disengage contact of the scraper shroud with the inner wall surface of a tube. Without the umbrella scraper in contact with the inner wall, insertion of the tube cleaner into a tube may be possible and the tube cleaner may be allowed rapid transit through the tube. With the arms extending so that the umbrella scraper is in contact with the inner wall surface of a tube or lumen, the tube cleaner may be translated along the length of the tube and act to scrape and catch mucus, biofilm, detritus, and other debris and undesirable buildup along the inner wall of the tube. In some embodiments, when expanded, the umbrella scraper may form a disc at the expansion portion. The disc may contact the tube wall and provide a surface with which to scrape biofilm, mucus, or other debris from the tube when the scraper is pulled in the lumen.

Furthermore, the translation sheath may be formed from a typical catheter, or may be formed of any suitable structure or material. The translation sheath and other scraper components may be comprised of plastic, metal, rubber, silicone, or any other suitable material, or any combination thereof. The translation sheath and other scraper components may have any cross-sectional shape, such as round or polygonal. The umbrella scraper may comprise an expansion portion that may expand into a disc having any suitable cross-sectional area, such as roughly square (i.e., if four frame ribs or petals are used) or approximately round (if many frame ribs or petals are used). The umbrella portion may be configured to contact an entire circumference of a lumen or inner surface of a tube, or may contact only a portion thereof. An umbrella portion configured to contact an entire circumference of a lumen or inner surface of a tube may provide a sealed extraction path from the point of deployment in a tube (such as a fluid conveyance tube, a waste discharge tube, or an ET tube) to the outside of such tube. For example, for cleaning an ET tube, the cleaning tube may be deployed in a sterile (closed) environment so as to avoid the need to disconnect an ET tube circuit, thus avoiding patient exposure to a non-sterile environment.

Such a scraper may be deployed to clean a variety of tubes and pipes. Tubes in a variety of industries and applications may become contaminated and require cleaning along the inside diameter of the tube. For tubes having one or more curves, the inside diameter may be difficult to access for adequate cleaning. In industries such as waste disposal, fluid transseat, food and beverage manufacturing, health care, and materials handling, for example, proper cleaning of tubes is often required to satisfy health, safety and environmental regulations. In the health care industry, for example, tubes are used to convey various fluids, such as medicine, IV solutions, or other types of fluids. In addition, tubes can be used to provide access channels, such as tubes used to provide access to artificial airways when a patient requires respiratory supseat. In these cases, tubes used in these environments may become contaminated and require periodic cleaning to avoid potential complications with patients.

Patients having damaged or challenged airways due, for example, to trauma or pathology or the inability to breathe unaided, may require the placement of an endotracheal tube. An endotracheal tube is used to supseat the patient's ventilatory requirements after major surgery, trauma, or the development of severe medical conditions affecting the patient's ability to breathe effectively.

Endotracheal intubation is a procedure that may be performed for a variety of clinical conditions and settings. It involves the placement of an artificial airway or endotracheal tube (ET tube) through the nose or mouth (orotracheal/nasotracheal tube) or directly through the trachea (tracheostomy tube) using a surgical procedure for insertion. The goal of an ET tube is to provide a clear path into a patient's lungs for proper intake of oxygen and removal of carbon dioxide when the patient requires additional breathing supseat. Patency of the ET tube is therefore essential to guarantee adequate gas exchange. However, since the ET tube is a foreign body, the airways may react by increasing production and buildup of mucus. These secretions have a tendency to accumulate and increase viscosity. In order to mitigate any issue related occlusion of the ET tube, periodic cleaning of artificial airways or endotracheal tubes is considered the standard of care on patients that require endotracheal intubation in a hospital or critical care setting. The endotracheal tube may be coupled to a mechanical ventilator to aid the patient's respiration, and may remain in place for short periods or for extended periods of time, such as until the patient is able to breathe independently. Such periods of times may be for hours, days, weeks or months.

Secretions, debris, mucus, or other biological materials (biofilm) may thus accumulate on the inside wall of the endotracheal tubes. Such accumulation often occurs shortly after (e.g., within 24 hours of) initial intubation. Biofilms may contain harmful bacteria from which infection can originate. Thus, use of an endotracheal intubation may be a significant risk factor for infections, such as ventilator-acquired pneumonia. Such infections and attendant risks significantly increase patient morbidity rates, complications, number of ventilator days, and the cost of hospitalization.

Moreover, it may not be practical or clinically acceptable to change out the endotracheal tube due to buildup of biofilm, or remove the tube for cleaning. Removal and reinsertion of the endotracheal tube may add to patient discomfort, injure the airway, and decrease control of the airway during such process. Accordingly, the disclosed scraper may be used to clean such a tube without removing the tube. However, an umbrella scraper as described above may be suitably configured for use in any body-inserted tube, as well as any tube in which buildup may occur, such as in plumbing drain lines. Thus, the cleaning tube is not limited to use in ET tubes. A method for cleaning a tube, such as an endotracheal tube, may comprise inserting the tube cleaner into the tube and then translating the tube cleaner the length of the tube at stopping prior to the exit point of the tube. Alternately, the tube cleaner may be stopped at any earlier area in the tube that may be in need of cleaning. This is to be done with the arms of the scraper armature in the retracted position.

With the tube cleaner in the desired location, the arms of the scraper armature may be extended until the umbrella scraper is applying force to the inner wall of the tube. With the leading edge of the umbrella scraper in contact with the inner wall, the tube cleaner may be translated along the length of the tube in a direction of travel toward the user and away from the patient.

Upon reaching the open end of the tube, the umbrella scraper may be replaced or cleaned and the process repeated until the tube reaches the desired level of cleanliness.

Although the disclosed subject matter and its advantages have been described in detail, it should be understood that various changes, substitutions and alterations can be made herein without departing from the tube cleaner as defined by the appended claims. Moreover, the scope of the claimed subject matter is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

We claim:

1. A scraper for cleaning a tube, the scraper comprising:
   a head comprising a cam guide surface;
   an expandable armature comprising a collar and a plurality of petals flexibly attached to the collar, at least one petal having a ridge configured to co-act with the cam guide surface, the collar translatably coupled to the head, the armature configured to co-act with the head so as to permit translation of the armature with respect to the head between a retracted position in which the petals rest against the head for insertion into a tube and a deployed position in which the petals are expanded radially away from the head; and
   an actuator coupled to the head, the actuator being manipulable to move the head so as to translate the armature between the retracted position and the deployed position.

2. The scraper of claim 1, comprising:
   the head comprising a round radial cross-section, and the cam guide surface comprising a conical portion of the head, the conical portion comprising a larger diameter and a smaller diameter;
   the ridge being disposed on the smaller diameter when the armature is in the retracted position, and disposed on the larger diameter when the armature is in the deployed position.

3. The scraper of claim 2, wherein the petals overlap.

* * * * *